United States Patent
Feith (10) Patent No.: US 12,379,037 B2
(45) Date of Patent: Aug. 5, 2025

(54) STEPPED CHECK VALVES

(71) Applicant: CareFusion 303, Inc., San Diego, CA (US)

(72) Inventor: Raymond P. Feith, Chino Hills, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 18/536,657

(22) Filed: Dec. 12, 2023

(65) Prior Publication Data

US 2024/0200675 A1 Jun. 20, 2024

Related U.S. Application Data (60) Provisional application No. 63/433,718, filed on Dec. 19, 2022.

(51) Int. Cl.
| | |
|---|---|
| *F16K 15/02* | (2006.01) |
| *F16K 27/02* | (2006.01) |
| *A61M 5/168* | (2006.01) |

(52) U.S. Cl.
CPC ........ *F16K 15/023* (2013.01); *F16K 27/0209* (2013.01); *A61M 5/16813* (2013.01)

(58) Field of Classification Search
CPC .......................... F16K 15/023; F16K 15/0209
See application file for complete search history.

(56) References Cited

U.S. PATENT DOCUMENTS

| | | | |
|---|---|---|---|
| 5,727,594 A | * 3/1998 | Choksi | .................. F16K 15/144 |
| | | | 137/859 |
| 11,248,719 B2 | 2/2022 | Maleki et al. | |
| 2007/0100295 A1 | * 5/2007 | Belley | .................. A61M 39/06 |
| | | | 604/246 |
| 2019/0093775 A1 | 3/2019 | Feith et al. | |
| 2019/0316695 A1 | 10/2019 | Feith et al. | |

FOREIGN PATENT DOCUMENTS

CN 113164732 A 7/2021

OTHER PUBLICATIONS

Chinese Office Action for Utility Model Application No. 202323453296.6, dated Jul. 19, 2024, 4 pages including translation.
International Search Report and Written Opinion for Application No. PCT/US2023/081431, dated Mar. 18, 2024, 9 pages.

* cited by examiner

*Primary Examiner* — P. Macade Nichols (57) ABSTRACT

A check valve includes an upper housing defining an inlet of the check valve, a lower housing defining an outlet of the check valve, and a cavity interposed between and defined by the upper and lower housings for fluidly connecting the inlet and the outlet. The check valve further includes a valve member mounted in the cavity to selectively permit fluid flow in a first direction, and prevent fluid backflow in a second direction opposite to the first direction. The valve member includes a valve body and a valve stem portion extending axially through a central axis of the valve body.

18 Claims, 5 Drawing Sheets

STEPPED CHECK VALVES

CROSS REFERENCE TO RELATED APPLICATION

This application claims the benefit of priority under 35 U.S.C. § 119 to U.S. Provisional Patent Application Ser. No. 63/433,718, entitled "STEPPED CHECK VALVES", filed on Dec. 19, 2022, the entire contents of which is incorporated herein by reference.

TECHNICAL FIELD

The present disclosure generally relates to check valves, and more particularly to conical stepped check valves having a geometry that allow for proper placement of the valve member during assembly. This optimizes backchecking capability.

BACKGROUND

Patients are commonly injected with IV solutions that are initially provided in an IV reservoir (a bottle or bag) and dripped into the vein of the patient through an IV line. Typically, an injection port is provided along the IV line and adapted to function with a syringe to permit an injectate to be added to the IV solution. A check valve is also commonly included in the IV line to permit fluid flow only in the direction of the patient. This ensures that the injectate flows downstream toward the patient, not upstream toward the IV reservoir.

SUMMARY

Many check valves utilize valve members, that may be shaped like a disc, that floats without being constrained before assembly. There are occasions when an offset disk will not completely close because the outer edge is hanging upon the inside wall. Failure to completely close prevents and compromises backchecking capability. The present disclosure generally relates to check valves, and more particularly to conical stepped check valves having a geometry that allows for proper placement of the valve member during assembly of the check valves.

In accordance with various embodiments of the present disclosure, a check valve includes an upper housing, a lower housing, a cavity interposed between and defined by the upper and lower housings, and a valve member mounted in the cavity to selectively permit fluid flow in a first direction and prevent fluid backflow in a second direction opposite to the first direction. The upper housing defines an inlet of the check valve, and the lower housing defines an outlet of the check valve. The cavity fluidly connects the inlet and the outlet.

In accordance with various embodiments of the present disclosure, a check valve includes an upper housing defining an inlet of the check valve, a lower housing axially coupled to the upper housing and comprising an outlet of the check valve, and a cavity interposed between and defined by the upper and lower housings for fluidly connecting the inlet and the outlet. The check valve further includes a flexible valve member mounted in the cavity to selectively permit fluid flow in a first direction and prevent fluid backflow in a second direction opposite to the first direction. In accordance with various embodiments of the present disclosure, a flexible valve member may be shaped like a disk.

Embodiments of the present disclosure provide a check valve, comprising an upper housing defining an inlet of the check valve, a lower housing defining an outlet of the check valve, wherein a cavity is interposed between and defined by the upper and lower housings for fluidly connecting the inlet and the outlet and a valve member seated in the cavity to selectively permit fluid flow in a first direction and restrict fluid backflow in a second direction opposite to the first direction.

In some embodiments, the check valve has a conical stepped geometry. In some embodiments, the conical stepped geometry prevents the valve member from touching an inner wall of the upper housing. In some embodiments, a sealing surface is defined at a distal end of the upper housing. In some embodiments, in a closed state, the valve member is configured to contact the sealing surface to limit fluid flow past the sealing surface. In some embodiments, the lower housing comprises a biasing post disposed in the cavity at a central portion thereof. In some embodiments, a central axis of the biasing post is aligned with a central longitudinal axis of the check valve and the valve member is configured to be seated on the biasing post. In some embodiments, when an upstream pressure is applied to the valve member, the valve member is configured to deflect away from the sealing surface to fluidly communicate the inlet and the cavity.

In some embodiments, when a downstream pressure is applied to the valve member, the valve member is configured to deflect towards the sealing surface to block the fluid communication between the inlet and the cavity. In some embodiments, when a downstream pressure is applied to the valve member, the valve member is restrict backflow of the fluid from the outlet to the inlet.

In some embodiments, the biasing post may include a central aperture and a two semi cylindrical slots through which fluid may flow from the inlet and into the cavity. In some embodiments, the valve member has a raised surface and a flat surface. In some embodiments, the check valve is generally tubular. In some embodiments, the valve member never touches an inner wall of the upper housing. In some embodiments, a central axis of the biasing post is coaxially aligned with a central longitudinal axis of the check valve. In some embodiments, the biasing post is coupled to, integrally formed with, or otherwise protrudes from an upstream internal surface of the lower housing.

Embodiments of the present disclosure provide a method for assembling a check valve, comprising providing an upper housing defining an inlet of the check valve, providing a lower housing defining an outlet of the check valve, wherein a cavity interposed between and defined by the upper and lower housings for fluidly connecting the inlet and the outlet and providing a valve member seated in the cavity to selectively permit fluid flow in a first direction, and restrict fluid backflow in a second direction opposite to the first direction, comprising placing the valve member in the upper housing and vibrating the valve member and upper housing until the valve member is fully seated in the upper housing.

In some embodiments, the check valve has a conical stepped geometry. In some embodiments, a sealing surface is defined at a distal end of the upper housing and in a closed state, the valve member is configured to contact the sealing surface to limit fluid flow past the sealing surface.

In some embodiments, the lower housing comprises a biasing post disposed in the cavity at a central portion thereof, a central axis of the biasing post being aligned with a central longitudinal axis of the check valve, and the valve member is configured to be seated on the biasing post.

In some embodiments, when an upstream pressure is applied to the valve member, the valve member is configured to deflect away from the sealing surface to fluidly communicate the inlet and the cavity and when a downstream pressure is applied to the valve member, the valve member is configured to deflect towards the sealing surface to block the fluid communication between the inlet and the cavity and to restrict backflow of the fluid from the outlet to the inlet.

It is to be understood that both the foregoing general description and the following detailed description are exemplary and explanatory and are intended to provide further explanation of the subject technology as claimed. It is also to be understood that other aspects may be utilized, and changes may be made without departing from the scope of the subject technology

BRIEF DESCRIPTION OF THE DRAWINGS

The following figures are included to illustrate certain aspects of the embodiments and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

The present description relates in general to check valves, and more particularly, for example and without limitation, to more particularly to conical stepped check valves having a geometry that allows for proper placement of the disk valve member during assembly of the check valves.

In some embodiments, the check valve is used in an IV administration set having a structure for coupling with an IV bag and/or a drip chamber. The structure for the IV bag can be formed as an arm, hook, clamp, or another mechanism configured to suspend the IV bag.

Figure 1:
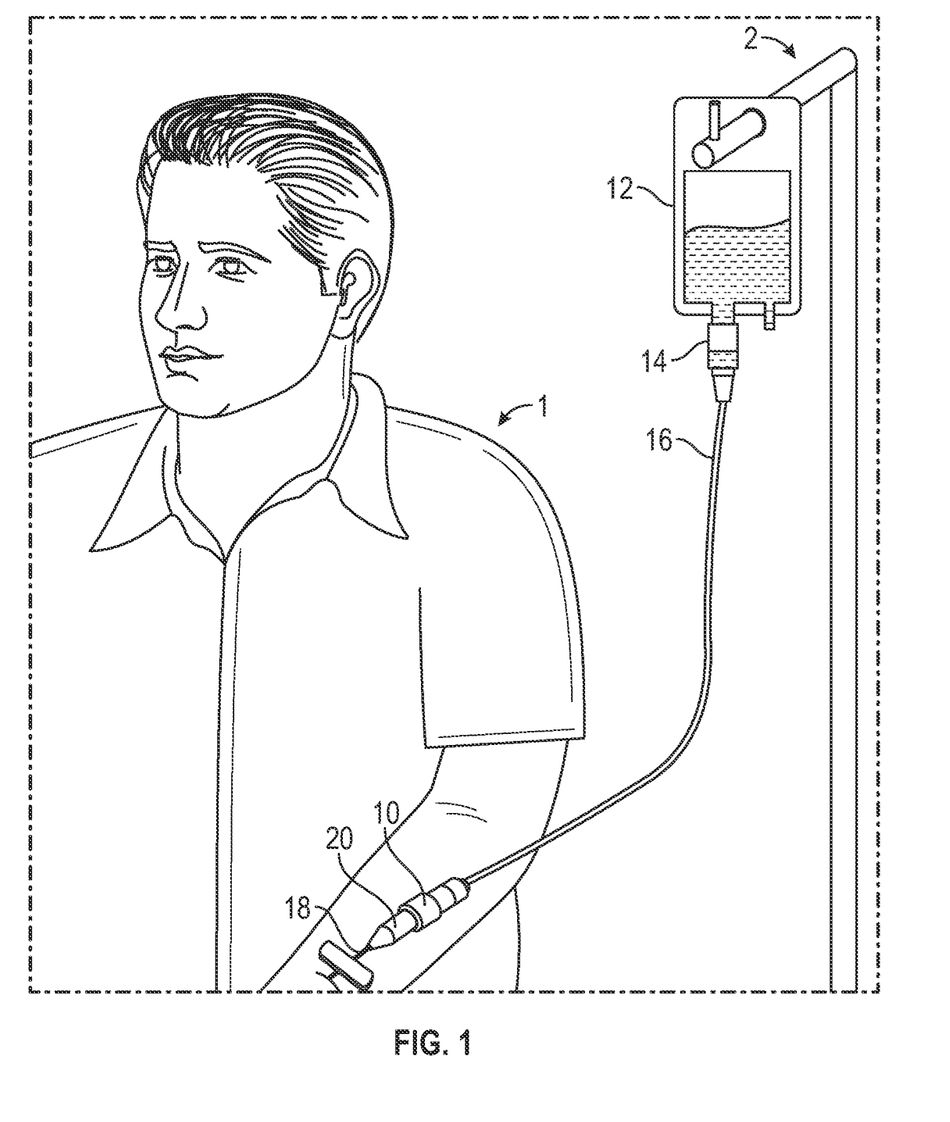
FIG. 1 illustrates an IV administration set coupled to a patient, in accordance with aspects of the present disclosure.

Referring to FIG. 1A, an embodiment of an IV administration set 2 is coupled to a patient 1. The IV administration set 2 includes a check valve 100. The IV administration set has an IV bag 12 and a drip chamber 14 fluidly coupled together by IV tubing 16 extending therebetween. The IV tubing is intravenously coupled to the patient 1 through a catheter 18, and the catheter preferably includes one or more adapters 10 or connectors 20.

Figure 2:
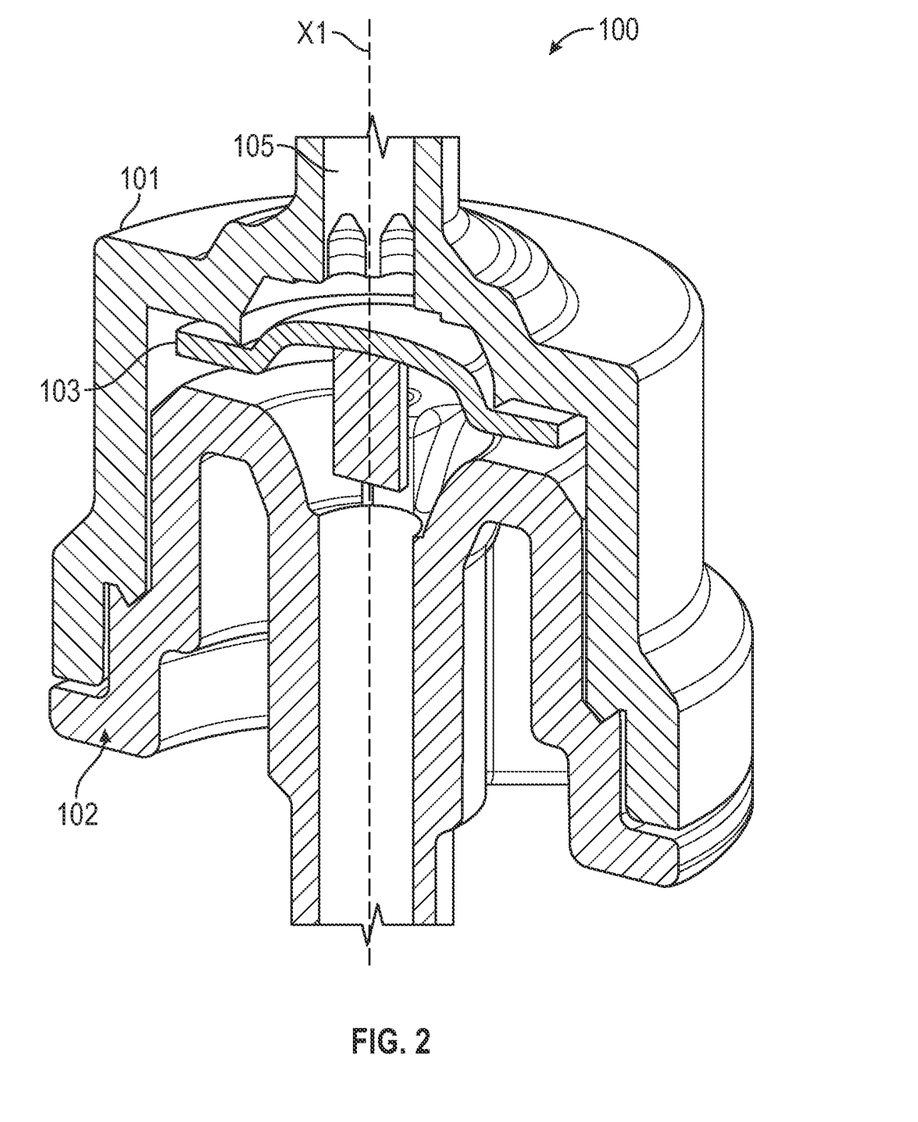
FIG. 2 is a perspective cross-sectional view of a check valve assembly, in accordance with some embodiments of the present disclosure.

FIG. 2 is a perspective cross sectional view of the conical stepped disk check valve, in accordance with some embodiments of the present disclosure. As depicted, a top portion of the check valve 100 (i.e., an upper housing 101) is displayed in cross-sectional view to illustrate some of the features of the check valve 100. Referring to FIG. 2, the check valve 100 includes an axially extending body 105 defining a central longitudinal axis X1. The body 105 may be a generally cylindrical (or tubular) structure and may include an upper housing 101 and a lower housing 102.

Figure 3A:
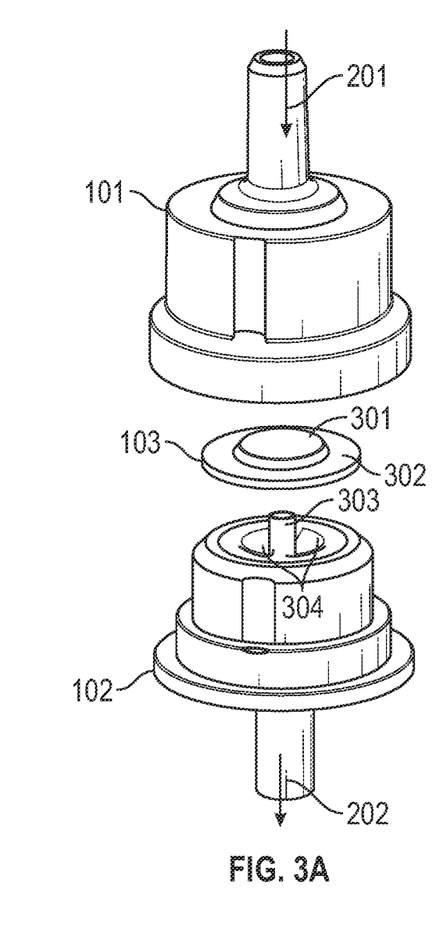
FIG. 3A is an exploded perspective view of the check valve assembly of FIG. 2, in accordance with some embodiments of the present disclosure.
Figure 3B:
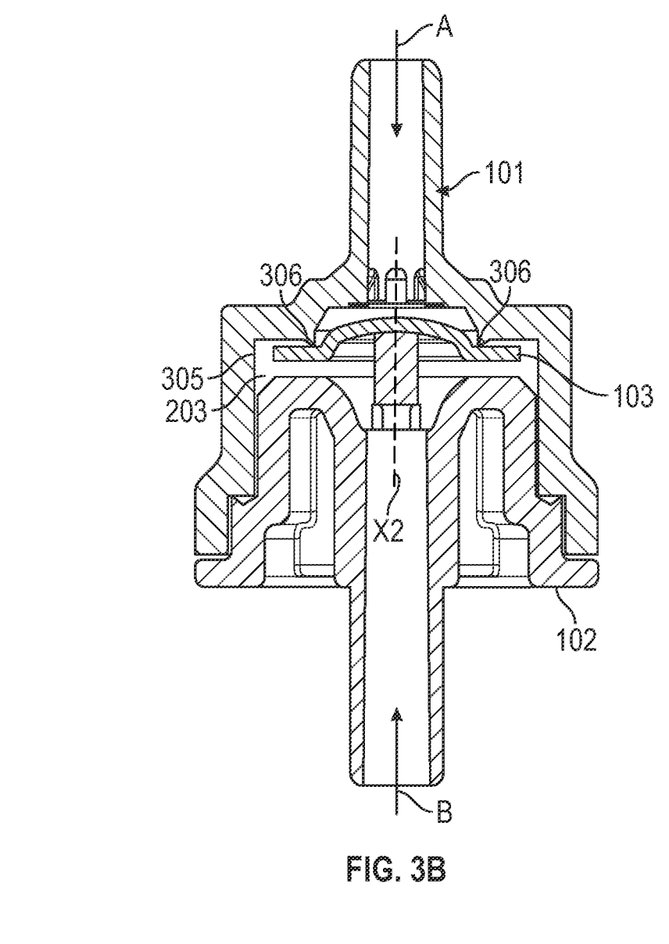
FIG. 3B is a cross-sectional view of the check valve assembly of FIG. 2, in accordance with some embodiments of the present disclosure.

As shown in FIGS. 3A-3B, the upper housing 101 may include an inlet 201 of the check valve 100 at the first end, and the lower housing 102 may include an outlet 202 of the check valve 100. The body 105 may define an internal flow passage 203 axially extending between the inlet 201 and the outlet 202 and in fluid communication therewith. The check valve 100 may permit fluid to flow from the inlet 201 to the outlet 202 (as indicated by arrow A), and minimize, or otherwise restrict or limit, fluid flow from the outlet 202 to the inlet 201 (as indicated by arrow B). As depicted, the upper housing 101 and the lower housing 102 may define the cavity 203 for fluidly connecting the inlet 201 and the outlet 202. In the depicted embodiments, the valve member 103 may be mounted in the cavity 203 to selectively permit fluid flow in the first direction (indicated by arrow A) and prevent fluid backflow (reverse flow) in the second direction opposite to the first direction (indicated by arrow B).

In accordance with some embodiments, the valve member 103 may have a raised surface 301 and a flat surface 302. The valve member 103 may be in the form of a disk or any other circular plate. As depicted, the valve member 103 may be seated on a biasing post 303 of the lower housing 102. In particular, the biasing post 303 may include a central aperture and a two semi cylindrical slots 304 through which fluid flowing from the inlet 201 and into the cavity 203 may enter the outlet 202 in an open state of the check valve 100.

Figure 4A:
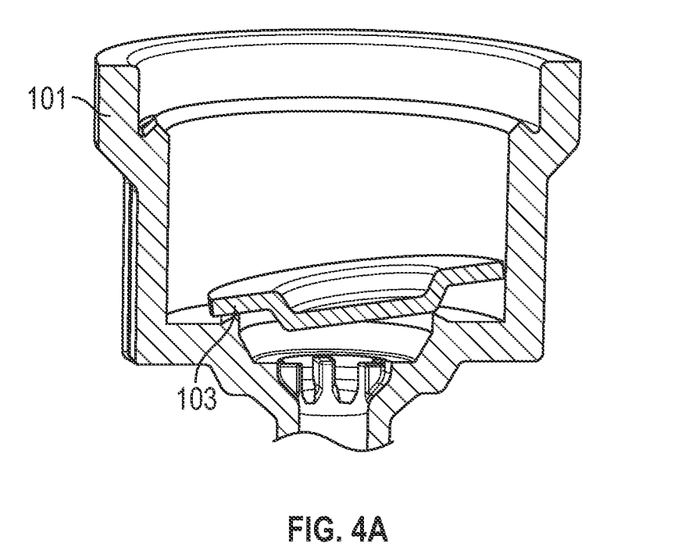
FIGS. 4A-4B illustrate the position of the disk valve in the upper housing of the check valve of FIG. 3, in accordance with some embodiments of the present disclosure.
Figure 4B:
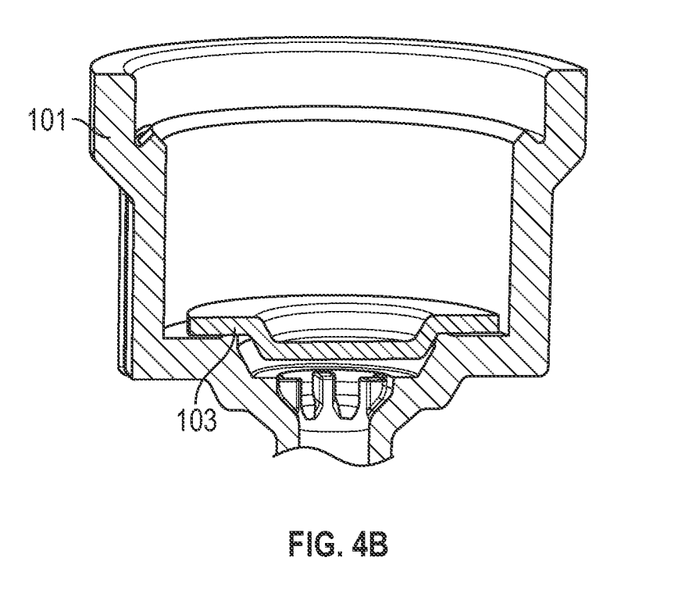

In accordance with some embodiments, the upper housing 101 and the lower housing 102 may have a conical stepped design. Referring to FIGS. 4A-4B, the conical stepped geometry will cause the valve member 103 to be closer to central axis of the check valve 100, thus preventing the valve member 103 from touching the inner wall 305 of the upper housing 101. This conical stepped geometry eliminates any possible friction between the inner wall 305 of the upper housing 101 and outer edge of the valve member 103. The assembly process may be designed to vibrate causing the valve member 103 to fall into the desired pocket of the upper housing 101. In this case, the valve member 103 cannot touch the inner wall 305 of the upper housing 101 and become hung up. The biasing post 303 of the lower housing holds the valve member 103 in place after assembly.

An identified issue experienced during packaging, transportation and assembly of some check valves is that when valve members (e.g., disc-type check valve members) are packaged in bulk and/or transported on a conveyance line, there are occasions when an offset disk will not completely close because the outer edge is hanging upon the inside wall. In particular, since some disc-type valve members are generally flat and made of silicone which, in some circumstances, may have a greater degree of stiction, the geometry of previous commercial designs allows for some disc-type valve members to stick to the inner wall 305 of the check valve 100 and not sit properly. This makes automated assembly difficult and prevents backchecking capability. As illustrated in FIGS. 4A-4B, the valve member 103 may be placed inside the upper housing 101. FIG. 4A shows the valve member 103 inside of the upper housing 101 in an inverted orientation as shown in FIGS. 3A-3B, but the valve member 103 is not seated properly. Upon insertion, the valve member 103 and upper housing 101 may be shaken or otherwise vibrated, which causes the valve member to fall into the correct place, as shown in FIG. 4B. The aforementioned conical stepped geometry of the check valve 100 may provide several manufacturing and assembly advantages.

Figure 5A:
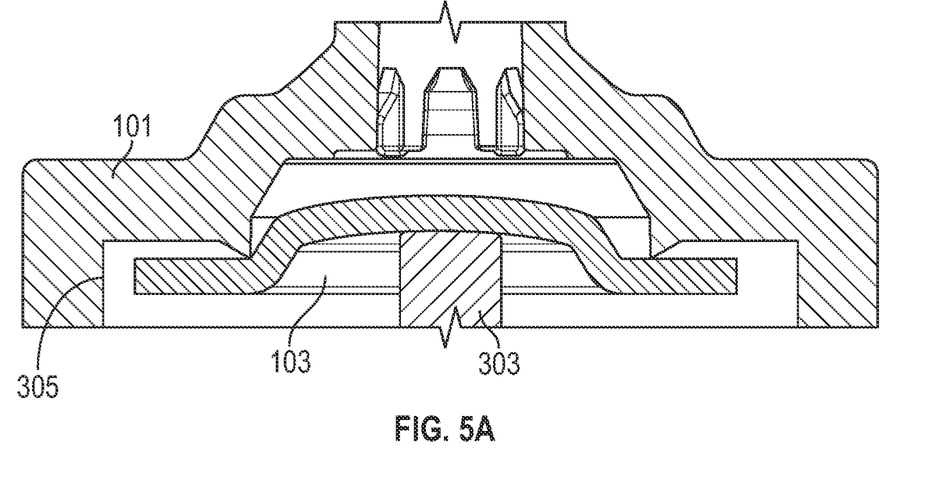
FIGS. 5A-5B are enlarged partial cross-sectional views of the check valve of FIG. 3, in accordance with some embodiments of the present disclosure.
Figure 5B:
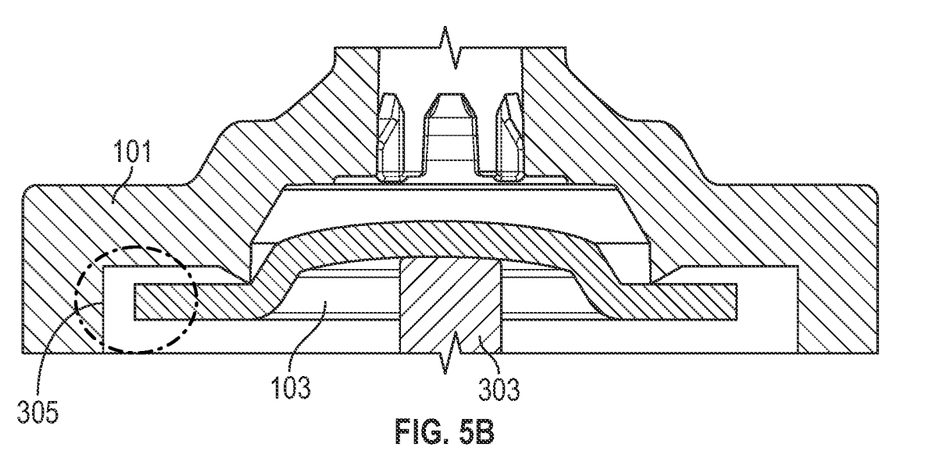

FIGS. 5A-5B show an enlarged cross-sectional view of the assembled stepped check valve. FIG. 5A shows the upper housing 101, the biasing post 303 of the lower housing 102, and the valve member 103 in concentric alignment. As illustrated in FIG. 5A, the valve member 103 is unable to touch the inner wall 305 of the upper housing 101. FIG. 5B shows the maximum possible offset that can occur between the upper housing 101, the biasing post 303 of the lower housing 102, and the valve member 103. As illustrated by the red circle, at maximum offset, the valve member 103 is still prohibited from touching the inner wall 305 of the upper housing 101.

Referring back to FIGS. 3A-3B, the biasing post 303 may be centrally disposed in the cavity 203, and a central axis X2 of the biasing post 303 may be coaxially aligned with the central longitudinal axis X1 of the check valve 100. The biasing post 303 may be coupled to, integrally formed with, or otherwise protrude from the upstream internal surface 52 of the lower housing 102 and extend into the cavity 203. As discussed in further detail below, the cavity 203 may form a part of the internal flow passage or may be otherwise fluidly communicated with the internal flow passage and therefore, fluid flowing from the inlet 201 to the outlet 202 may flow via the cavity 203.

FIG. 3B is a cross-sectional view of check valve 100, in accordance with some embodiments of the present disclosure in the closed state, wherein the check valve 100 restricts fluid flow in the reverse directions. As depicted, the upper housing 101 may include the internal surface 305 extending along the length of the interior of the upper housing 101 and defining the flow passage 203. As illustrated in FIG. 3B, in the normally closed state of the check valve 100, the valve member 103 contacts the sealing surface 306, reverse flow (backflow, arrow B) of fluid from the outlet 202 to the inlet 201 is restricted or prevented. The geometry of the valve member has a raised portion 301 and a flat portion 302. Backflow fluid causes the outer flat portion 302 of the valve member 103 to deflect and seal off the flow passage in the upper housing, further described below.

During operation, when a downstream pressure (i.e., a pressure applied by a fluid flowing from the outlet 202 to the inlet 201 is applied to the valve member 103, the valve member 103 may deflect towards the sealing surface 306 to block or restrict the fluid communication between the inlet 201 and the cavity 203, thereby restricting backflow of the fluid from the outlet 202 to the inlet 201. Preventing or restricting backflow of the fluid is advantageous in that it restricts undesirable particulate matter, as one example, that may be contained in a drug dispensed from a secondary path from flowing back through the check valve 100, thereby preventing the patient from receiving the proper drug dosage concentration or from timely delivery of the drug.

In accordance with some embodiments, the valve member 103 may be formed of a flexible, resilient material which is fluid impervious. For example, the valve members 103 may be made of a silicon material. In other embodiments, however, the valve member 103 may be formed of any non-sticking, resilient material such as natural or synthetic rubber or polymers. The valve member 103 may be formed of a material having a shore hardness of 70 or less.

In some embodiments, the valve member 103 are not limited to any particular shape or size. In the depicted embodiments, however, the size of the valve member 103 may be limited so that it will never touch the inner wall 305 of the upper housing during assembly. The size of the valve member 103 may also be limited based on desired deflection/bending characteristics of the valve member 103 when subjected to either of the upstream or downstream forces. For example, the valve member 103 may be sized and shaped so as to flex or bend under fluid pressure to permit forward flow (from the inlet 201 to the outlet 202) of the fluid into the cavity 203, and to limit fluid flow in the reverse direction.

In the open state of the check valve 100, for example when subjected to an upstream pressure (i.e., a pressure applied by a fluid flowing from the inlet 201 to the outlet 202), the check valve 100 permits fluid flow in the forward direction (direction of inlet 201 to outlet 202). During operation, fluid may enter the check valve 100 via the inlet 201 into the cavity 203. The upstream pressure (i.e., pressure applied by fluid flowing from the inlet 201 to the outlet 202) applied to the valve member 103 causes the valve member 103 to bow or bend downwards at the outer edges thereof and deflect away from the sealing surface 306.

Various examples of aspects of the disclosure are described as numbered clauses (1, 2, 3, etc.) for convenience. These are provided as examples and do not limit the subject technology. Identification of the figures and reference numbers are provided below merely as examples for illustrative purposes, and the clauses are not limited by those identifications.

Clause 1: A check valve, comprising an upper housing defining an inlet of the check valve, a lower housing defining an outlet of the check valve, wherein a cavity is interposed between and defined by the upper and lower housings for fluidly connecting the inlet and the outlet, and a valve member seated in the cavity to selectively permit fluid flow in a first direction and restrict fluid backflow in a second direction opposite to the first direction.

Clause 2: The check valve of Clause 1, wherein the check valve has a conical stepped geometry.

Clause 3: The check valve of Clause 2, wherein the conical stepped geometry prevents the valve member from touching an inner wall of the upper housing.

Clause 4: The check valve of Clause 1, wherein a sealing surface is defined at a distal end of the upper housing.

Clause 5: The check valve of Clause 4, wherein in a closed state, the valve member is configured to contact the sealing surface to limit fluid flow past the sealing surface.

Clause 6: The check valve of Clause 1, wherein the lower housing comprises a biasing post disposed in the cavity at a central portion thereof.

Clause 7: The check valve of Clause 6, wherein a central axis of the biasing post is aligned with a central longitudinal axis of the check valve and the valve member is configured to be seated on the biasing post.

Clause 8: The check valve of Clause 1, wherein when an upstream pressure is applied to the valve member, the valve member is configured to deflect away from the sealing surface to fluidly communicate the inlet and the cavity.

Clause 9: The check valve of Clause 1, wherein when a downstream pressure is applied to the valve member, the valve member is configured to deflect towards the sealing surface to block the fluid communication between the inlet and the cavity.

Clause 10: The check valve of Clause 1, wherein when a downstream pressure is applied to the valve member, the valve member is configured restrict backflow of the fluid from the outlet to the inlet.

Clause 11: The check valve of Clause 6, wherein the biasing post may include a central aperture and a two semi cylindrical slots through which fluid may flow from the inlet and into the cavity.

Clause 12: The check valve of Clause 1, wherein the valve member has a raised surface and a flat surface.

Clause 13: The check valve of Clause 1, wherein the check valve is generally tubular.

Clause 14: The check valve of Clause 1, wherein the valve member never touches an inner wall of the upper housing.

Clause 15: The check valve of Clause 6, wherein a central axis of the biasing post is coaxially aligned with a central longitudinal axis of the check valve.

Clause 16: The check valve of Clause 6, wherein the biasing post is coupled to, integrally formed with, or otherwise protrudes from an upstream internal surface of the lower housing.

Clause 17: A method for assembling a check valve, comprising providing an upper housing defining an inlet of the check valve, providing a lower housing defining an outlet of the check valve, wherein a cavity interposed between and defined by the upper and lower housings for fluidly connecting the inlet and the outlet, and providing a valve member seated in the cavity to selectively permit fluid flow in a first direction, and restrict fluid backflow in a second direction opposite to the first direction, comprising placing the valve member in the upper housing and vibrating the valve member and upper housing until the valve member is fully seated in the upper housing.

Clause 18: The method of Clause 17, wherein the check valve has a conical stepped geometry.

Clause 19: The method of claim 18, wherein a sealing surface is defined at a distal end of the upper housing and in a closed state, the valve member is configured to contact the sealing surface to limit fluid flow past the sealing surface.

Clause 20: The method of claim 18, wherein the lower housing comprises a biasing post disposed in the cavity at a central portion thereof, a central axis of the biasing post being aligned with a central longitudinal axis of the check valve and the valve member is configured to be seated on the biasing post.

Clause 21: The method of claim 18, wherein when an upstream pressure is applied to the valve member, the valve member is configured to deflect away from the sealing surface to fluidly communicate the inlet and the cavity and when a downstream pressure is applied to the valve member, the valve member is configured to deflect towards the sealing surface to block the fluid communication between the inlet and the cavity and to restrict backflow of the fluid from the outlet to the inlet.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A check valve, comprising:
   an upper housing defining an inlet of the check valve;
   a lower housing defining an outlet of the check valve, wherein a cavity is interposed between and defined by the upper housing and lower housing for fluidly connecting the inlet and the outlet; and
   a valve member seated in the cavity to selectively permit fluid flow in a first direction and restrict fluid backflow in a second direction opposite to the first direction,
   wherein the lower housing comprises a biasing post disposed in the cavity at a central portion thereof, and
   wherein the biasing post may include a central aperture and a two semi cylindrical slots through which fluid may flow from the inlet and into the cavity.

2. The check valve of claim 1, wherein the check valve has a conical stepped geometry.

3. The check valve of claim 2, wherein the conical stepped geometry prevents the valve member from touching an inner wall of the upper housing.

4. The check valve of claim 1, wherein a sealing surface is defined at a distal end of the upper housing.

5. The check valve of claim 4, wherein in a closed state, the valve member is configured to contact the sealing surface to limit fluid flow past the sealing surface.

6. The check valve of claim 1, wherein a central axis of the biasing post is aligned with a central longitudinal axis of the check valve and the valve member is configured to be seated on the biasing post.

7. The check valve of claim 4, wherein when an upstream pressure is applied to the valve member, the valve member is configured to deflect away from the sealing surface to fluidly communicate the inlet and the cavity.

8. The check valve of claim 4, wherein when a downstream pressure is applied to the valve member, the valve member is configured to deflect towards the sealing surface to block fluid communication between the inlet and the cavity.

9. The check valve of claim 1, wherein when a downstream pressure is applied to the valve member, the valve member is configured restrict backflow of the fluid from the outlet to the inlet.

10. The check valve of claim 1, wherein the valve member has a raised surface and a flat surface.

11. The check valve of claim 1, wherein the check valve is generally tubular.

12. The check valve of claim 1, wherein the valve member never touches an inner wall of the upper housing.

13. The check valve of claim 1, wherein a central axis of the biasing post is coaxially aligned with a central longitudinal axis of the check valve.

14. The check valve of claim 1, wherein the biasing post is coupled to, integrally formed with, or otherwise protrudes from an upstream internal surface of the lower housing.

15. A method for assembling a check valve, comprising:
    providing an upper housing defining an inlet of the check valve;
    providing a lower housing defining an outlet of the check valve, wherein a cavity interposed between and defined by the upper and lower housings for fluidly connecting the inlet and the outlet; and
    providing a valve member seated in the cavity to selectively permit fluid flow in a first direction, and restrict fluid backflow in a second direction opposite to the first direction, comprising:
    placing the valve member in the upper housing and vibrating the valve member and upper housing until the valve member is fully seated in the upper housing,
    wherein the lower housing comprises a biasing post disposed in the cavity at a central portion thereof, a central axis of the biasing post being aligned with a central longitudinal axis of the check valve, and
    wherein the biasing post may include a central aperture and a two semi cylindrical slots through which fluid may flow from the inlet and into the cavity.

16. The method of claim 15, wherein:
    a sealing surface is defined at a distal end of the upper housing; and in a closed state, the valve member is configured to contact the sealing surface to limit fluid flow past the sealing surface.

17. The method of claim 15, wherein
the valve member is configured to be seated on the biasing post.

18. The method of claim 16, wherein:
when an upstream pressure is applied to the valve member, the valve member is configured to deflect away from the sealing surface to fluidly communicate the inlet and the cavity; and
when a downstream pressure is applied to the valve member, the valve member is configured to deflect towards the sealing surface to block the fluid communication between the inlet and the cavity and to restrict backflow of the fluid from the outlet to the inlet.

* * * * *